(12) United States Patent
Nelson et al.

(10) Patent No.: US 6,849,397 B2
(45) Date of Patent: Feb. 1, 2005

(54) LABEL-FREE DETECTION OF NUCLEIC ACIDS VIA SURFACE PLASMON RESONANCE

(75) Inventors: Bryce P. Nelson, Madison, WI (US); Mark R. Liles, Madison, WI (US); Kendra Frederick, Madison, WI (US); Robert M. Corn, Madison, WI (US); Robert M. Goodman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 236 days.

(21) Appl. No.: 09/998,551

(22) Filed: Nov. 29, 2001

(65) Prior Publication Data

US 2003/0049639 A1 Mar. 13, 2003

Related U.S. Application Data

(60) Continuation-in-part of application No. 09/456,038, filed on Dec. 3, 1999, now Pat. No. 6,489,102, which is a division of application No. 09/368,991, filed on Aug. 5, 1999, now Pat. No. 6,127,129.
(60) Provisional application No. 60/132,342, filed on May 4, 1999.

(51) Int. Cl.[7] ............................ C12Q 1/70; C12Q 1/68; C12P 13/14
(52) U.S. Cl. ................................ 435/5; 435/6; 435/110
(58) Field of Search .................................. 435/6, 5, 110

(56) References Cited

U.S. PATENT DOCUMENTS

| 5,374,563 A | | 12/1994 | Maule |
| 5,629,213 A | | 5/1997 | Kornguth et al. |
| 5,837,832 A | * | 11/1998 | Chee et al. ................. 536/22.1 |
| 6,060,237 A | | 5/2000 | Nygren et al. |
| 6,127,129 A | | 10/2000 | Corn et al. |
| 6,228,580 B1 | | 5/2001 | Blumenfeld et al. |
| 6,232,068 B1 | * | 5/2001 | Linsley et al. ................. 435/6 |
| 6,472,148 B1 | * | 10/2002 | Bamdad et al. ................. 435/6 |
| 6,537,749 B2 | | 3/2003 | Kuimelis et al. |
| 6,579,726 B1 | | 6/2003 | Natan et al. |

FOREIGN PATENT DOCUMENTS

EP        0 305 108 A2    3/1989

OTHER PUBLICATIONS

Amann et al. (1990) Fluorescent–Oligonucleotide Probing of Whole Cells for Determinative, Phylogenetic, and Environmental Studies in Microbiology, *J. Bacteriol.* 172:762–770.

Anderson et al. (2000) Fabrication of Topologically Complex Three–Dimensional Microfluidic Systems in PDMS by Rapid Prototyping, *Anal. Chem.* 72:3158–3164.

Brockman et al. (1999) A Multistep Chemical Modification Procedure to Create DNA Arrays on Gold Surfaces for the Study of Protein—DNA Interactions with Surface Plasmon Resonance Imaging, *J. Am. Chem. Soc.* 121:8044–8051.

(List continued on next page.)

*Primary Examiner*—Jezia Riley
(74) *Attorney, Agent, or Firm*—Joseph T. Leone, Esq.; DeWitt Ross & Stevens S.C.

(57) ABSTRACT

Disclosed is a method to detect unlabeled nucleic acids (DNA and/or RNA) in a taxa, species, and organelle-specific fashion using surface plasmon resonance (SPR) imaging. Taxa-specific, species-specific, or organelle-specific nucleic acids are affixed to an SPR-suitable substrate. A nucleic acid sample to be analyzed is then contacted with the SPR-substrate and the substrate analyzed to determine the presence or absence of specific hybridization between the nucleic acids bound to the substrate and the nucleic acids contained in the sample. The method does not require that either the bound nucleic acids nor the sample nucleic acids be labeled. The method can be used to identify the source of nucleic acids, their sequence, as well as to identify organisms and place them within a given taxonomic hierarchy.

26 Claims, 4 Drawing Sheets-

OTHER PUBLICATIONS

Brockman et al. (2000) Surface Plasmon Resonance Imaging Measurements of Ultrathin Organic Films, *Ann. Rev. Phys. Chem.* 51:41:63.

Duffy et al. (1998) Rapid Prototyping of Microfluidic Systems in Poly(dimethylsiloxane) *Anal. Chem.* 70:4974–4984.

Effenhauser et al. (1997) Integrated Capillary Electrophoresis on Flexible Silicone Microdevices: Analysis of DNA Restriction Fragments and Detection of Single DNA Molecules on Microchips, *Anal. Chem.* 69:3451–3457.

FODOR (1997) *Science* 277:393–395.

Frutos et al. (1997) Demonstration of a word design strategy for DNA computing on surfaces, *Nucleic Acids Res.* 25:4748–4757.

Frutos et al (1998) Enzymatic Ligation Reactions of DNA "Words" on Surfaces for DNA Computing, *J. Am. Chem. Soc.* 120:10277–10282.

Frutos et al. (1998) SPR of Ultrathin Organic Films, *Anal. Chem.* 70:449A–455A.

Frutos et al. (2000) Reversible Protection and Reactive Patterning of Amine–and Hydroxyl–Terminated Self–Assembled Monolayers on Gold Surfaces for the Fabrication of Biopolymer Arrays, *Langmuir* 16:2192–2197.

Hickel et al. (1989) Surface–plasmon microscopy, *Nature* 339:186.

Jordan et al. (1997) Surface Plasmon Resonance Imaging Measurements of DNA Hybridization Adsorption and Streptavidin/DNA Multilayer Formation at Chemically Modified Gold Surfaces, *Anal. Chem.* 69:4939–4947.

Jordan et al. (1997) *Anal Chem.* 69(7):1449–1456.

Lockhart, et al. (1996) Expression monitoring by hybridization to high–density oligonucleotide arrays, *Nature Biotechnology* 14:1675–1680.

Nelson et al. (1999) Near–Infrared Surface Plasmon Resonance Measurements of Ultrathin Films. 1. Angle Shift and SPR Imaging Experiments, *Anal. Chem.* 71:3928–3934.

Nelson et al. (2001) Surface Plasmon Resonance Imaging Measurements of DNA and RNA Hybridization Adsorption onto DNA Microarrays, *Anal. Chem.* 73:1–7.

Pease et al. (1994) Light–generated oligonucleotide arrays for rapid DNA sequence analysis, *Proc. Natl. Acd. Sci. USA* 91:5022–5026.

Rothenhäusler&Knoll (1988) Surface–Plasmon microscopy, *Nature* 332:615–617.

Silin & Plant (1997) Biotechnological applications of surface plasmon resonance, *Trends in Biotechnol.* 15.

Strother et al. (2000) Covalent attachment of oligodeoxyribonucleotides to amine–modified Si (001) surfaces, *Nucleic Acids Research* 28:3535–3541.

Tarlov et al. (1993) UV Photopatterning of Alkanethiolate Monolayers Self–Assembled on Gold and Silver, *J. Am. Chem. Soc.* 115:5305–5306.

Thiel et al. (1997) In Situ Surface Plasmon Resonance Imaging Detection of DNA Hybridization to Oligonucleotide Arrays on Gold Surfaces, *Anal Chem.* 69:4948–4956.

Thomas et al. (1995) Probing Adhesion Forces at the Molecular Scale, *J. Am. Chem. Soc.* 117:3830–3834.

Winzeler et al. (1998) Direct Allelic Variation Scanning of the Yeast Genome, *Science* 281:1194–1197.

* cited by examiner

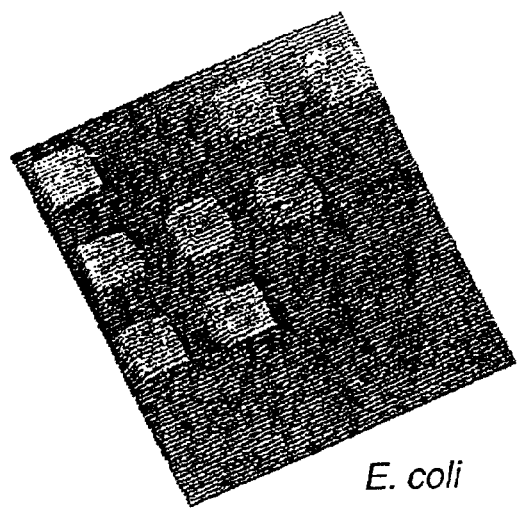
E. coli
Fig. 2A
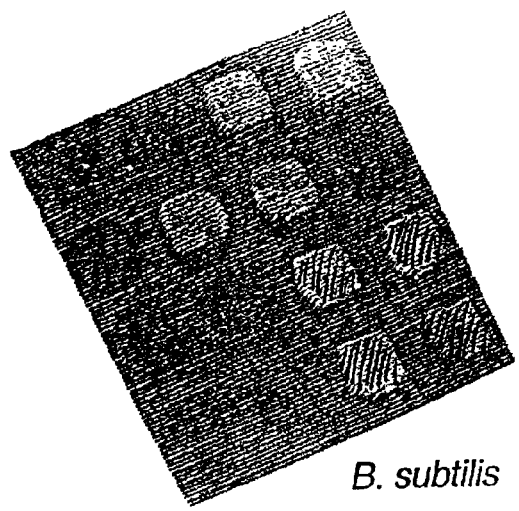
B. subtilis
Fig. 2B
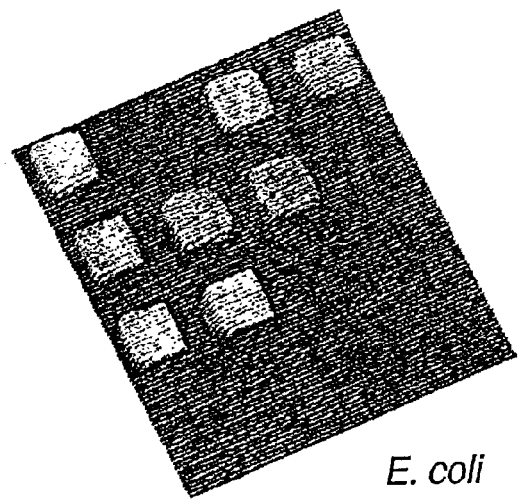
E. coli
Fig. 2C
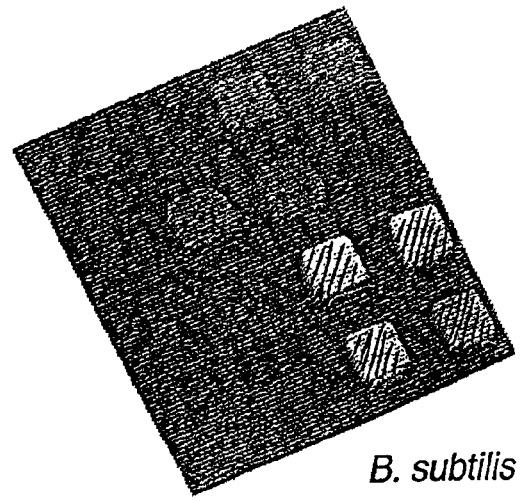
B. subtilis
Fig. 2D
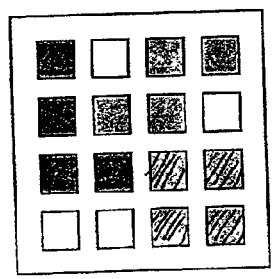
■ E. coli Probe, E186
▨ B. subtilis Probe, B491
▦ Universal Probe, EUB342
☐ Negative Control, NC

LABEL-FREE DETECTION OF NUCLEIC ACIDS VIA SURFACE PLASMON RESONANCE

This is a continuation-in-part of application Ser. No. 09/456,038, filed Dec. 3, 1999, now U.S. Pat. No. 6,489,102 which is a divisional of Ser. No. 09/368,991, filed 5 Aug. 1999 and issued 3 Oct. 2000 as U.S. Pat. No. 6,127,129, which claims priority to provisional application Ser. No. 60/132,342, filed May 4, 1999, all of which are incorporated herein by reference.

This invention was made with United States government support awarded by the National Institutes of Health, Grant No: NIH GM59622. The United States has certain rights in this invention.

FIELD OF THE INVENTION

The invention is directed to methods of identifying organisms and the source of nucleic acids in a taxa-specific and species-specific fashion.

DESCRIPTION OF THE RELATED ART

The binding of proteins to DNA plays a pivotal role in the regulation and control of gene expression, replication and recombination. In addition, enzymes that recognize and modify specific oligonucleotide sequences are critical components of biological nucleic acid manipulation and repair systems. An enhanced understanding of how these proteins recognize certain oligonucleotide sequences would aid in the design of biomedical systems which could, for example, be used to regulate the expression of therapeutic proteins. For this reason, the study of protein-nucleic acid interactions (i.e., protein-DNA and protein-RNA interactions) is a rapidly growing area of molecular biology, aided in part by recent advances in NMR and X-ray structural determination methods. At the same time, the explosive increase in the amount of available genomic and extra-genomic (i.e., ribosomal) sequence information obtained from large-scale nucleic acid sequencing efforts creates a need to survey this vast amount of new sequence data for protein binding sites. The present invention addresses this need by using surface plasmon resonance (SPR) imaging techniques as a rapid and efficient method for screening the sequence or structure-specific binding of proteins, DNA, or RNA to large arrays of nucleic acid molecules immobilized at chemically-modified metal surfaces.

Arrays of DNA molecules attached to planar surfaces are currently employed in hybridization adsorption experiments to sequence DNA, Pease et al. (1994); to screen for genetic mutations, Winzeler et al. (1998): and in DNA computing applications, Frutos et al. (1997) and Frutos et al. (1998) (*J. Am. Chem. Soc.*). These arrays are exposed to solutions containing fluorescently labeled complementary DNA sequences, rinsed, and then "read-out" using fluorescence imaging methods.

The technique of surface plasmon resonance (SPR) is a surface-sensitive, optical detection method well suited to the monitoring of reversible, protein-nucleic acid interactions.

The commercially successful "BIAcore" SPR instrument (Biacore AB, Uppsala, Sweden) has been used previously, for example, to study the interaction of DNA molecules with various enzymes. Although powerful, the "BIAcore" instrument has no imaging capabilities. This severely limits the number of DNA sequences that can be screened in a single experiment.

Surface plasmon resonance (SPR) is a surface optical technique which is sensitive to the thickness and index of refraction of material at the interface between a free electron metal (e.g., gold, silver, copper, cadmium, aluminum) and a bulk medium, such as air or water. Surface plasmon resonance may be achieved by using the evanescent wave which is generated when a laser beam linearly polarized parallel to the plane of incidence impinges onto a prism coated with a thin metal film. The metal may also be coated onto a thin transparent substrate such as glass, and this glass brought into optical contact with the prism. SPR is most easily observed as a reduction of the total internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of materials on top of the metal layer.

In using SPR to test for biological, biochemical, or chemical substances, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical, or chemical substance. The organic film can contain substances (such as antibodies, antigens, DNA, RNA, etc.) which can bind with an analyte in a sample to cause an increased thickness which will shift the SPR angle. By monitoring either the position of the SPR angle or the reflectivity at a fixed angle near the SPR angle, the presence or absence of an analyte in the sample can be detected.

Various types of equipment for using SPR with a biosensor for biological or biochemical or chemical substances are described by the Liedberg et al. article found in "Sensors and Actuators," Vol. 4, 1983, page 299. See also European Patent Application 0 305 108 and U.S. Pat. No. 5,374,563.

The use of conventional SPR as a testing tool offers several advantages and disadvantages. For example, it is relatively fast, it requires no labeling, and it can be performed on site. However, as noted above, commercially-available devices, such as the "BIAcore" instrument, offer no imaging capabilities. Additionally, to achieve the high through-put demanded by large-scale users, there is a need for a simple, practical biosensor which can be readily modified or adapted to test a wide variety of compounds simultaneously.

In SPR imaging, a light source (typically a monochromatic, incoherent, near-infrared light source) is used to illuminate a prism/thin gold film sample assembly at an incident angle that is near the SPR angle, and the reflected light is detected at a fixed angle with a CCD camera to produce an SPR image. The SPR image arises from variations in the reflected light intensity from different parts of the sample; these variations are created by any changes in organic film thickness or index of refraction that occur upon adsorption onto the modified gold surface. Since SPR imaging is sensitive only to molecules in close proximity to the surface (within ~200 nm), unbound molecules remaining in solution do not interfere with in situ measurements.

The formation of robust, reproducible arrays of oligonucleotides tethered to metal-coated surfaces (most often gold) is an essential requirement for SPR imaging of protein-nucleic acid binding interactions. To use SPR imaging techniques, it is essential that the nucleic acid array be constructed on a noble metal surface, and for this reason DNA arrays on glass supports from commercially available sources such as Affymetrix (Santa Clara, Calif.) are not a viable option. Using self-assembled monolayers of substituted alkanethiols as a starting point, others have previously developed schemes to attach single-stranded DNA molecules to chemically modified gold surfaces. See, for instance, U.S. Pat. No. 5,629,213). In the subject invention, however, micro-fluidic techniques are brought to bear to allow micro-arrays to be assembled in a site-directed manner on the metal surface, thereby enabling the creation of multi-component one-dimensional and two-dimensional arrays.

Nucleic acid array technology itself has revolutionized the practice of life sciences research, providing quantitative information on complex biological systems in a fraction of the time required by traditional methods. However, the application of such technology for quantitative measurement of biomolecules has been limited by the high costs and laborious techniques associated with radioactive and fluorescent labeling and detection (Lockhart et al. (1996); Fodor (1997)).

Micro-array technology was developed as a faster, easier, fluorescence-based detection method. However the current techniques remain impractical for large-scale screening of biomolecules, primarily because these techniques are time-consuming and often prohibitively expensive. Current micro-array techniques also require large amounts of chemicals in the fabrication process, and cannot detect the small volumes often used in molecular biology laboratories. Thus, there remains a need for a fast, simple, inexpensive, and reusable micro-array technology for large-scale screening of biomolecules.

SPR imaging is a surface optical technique that has been used extensively to measure binding of biological molecules onto chemically and biologically modified surfaces, Brockman et al. (2000). SPR imaging allows multiple molecular probes to be analyzed simultaneously for affinity to a target molecule or mixtures of target molecules. Brockman et al. (1999); Nelson et al. (2001). SPR imaging has been used for the analysis of DNA hybridization, Jordan et al. (1997); Thiel et al. (1997), the detection of RNA oligonucleotide hybridization, and DNA-protein interactions, Brockman et al. (1999); Brockman et al. (2000); Frutos et al. (2000).

SPR can be coupled with the use of near-infrared (NIR) excitation. This technique results in improved image contrast and better sensitivity over the more commonly used excitation from a beam-expanded visible laser, Nelson et al. (1999). A NIR-SPR imager device uses light from a collimated white light source to illuminate a high index glass prism at a fixed angle. A gold-coated glass slide containing a nucleic acid array is optically coupled to the prism. Using UV-photopatterning techniques, Tarlov et al. (1993), gold surfaces are chemically modified to create spatial arrays of molecules for use with SPR imaging (see U.S. Pat. No. 6,127,129). Light at 800 nm interacts with the patterned thin film from behind, creating surface plasmons. Reflectivity of the incident light is attenuated upon the creation of the surface plasmons; the momentum of these surface plasmons is determined by the index of refraction very close to the gold film. Adsorption of molecules such as nucleic acids onto the surface affects the index of refraction very close to the surface, thereby causing a change in the reflectivity of incident light. These changes in reflectivity are monitored with a CCD camera.

Overall, the new technology described herein gives researchers (i) a means of high-through put screening; (ii) permits the detection of biomolecule interactions using SPR imaging measurements in relatively small reaction volumes; and (iii) allows the simultaneous detection of multiple hybridization reactions during SPR experiments.

SUMMARY OF THE INVENTION

The present invention is a method for detecting unlabeled target nucleic acids (DNA and RNA) using a reusable array of immobilized probe nucleic acids. The immobilized probe nucleic acids are immobilized on a surface plasmon resonance-capable substrate and detection of the target nucleic acids is accomplished by measuring the change in refractive index near the surface of the substrate after contacting the substrate with a solution suspected of containing the target nucleic acids. The change in refractive index near the surface of the substrate is measured via surface plasmon resonance (SPR) techniques.

Hybridization of the target nucleic acids to the immobilized probe nucleic acids occurs in a sequence-specific fashion, thus allowing the method to be used in any number of applications where sequence-specific binding is required. For example, the method is useful for measuring the expression of specific genes in an organism. Because a specific gene will generate specific mRNAs and cDNAs, complementary nucleic acid probes can be generated and immobilized in an array to the SPR substrate. Cell extracts containing nucleic acids (RNA, DNA, or both) are then contacted with the array and the change in the refractive index of the array measured by SPR.

Likewise, the method is useful for identifying the source of DNA or RNA by using species- or taxon-specific probes immobilized on the SPR substrate. As described in full in the Examples, rRNA can be probed as target nucleic acid using an array of DNA complementary to the target rRNA. As shown in the examples, total RNA easily isolated from cellular samples can be matched with its source organism using SPR imaging. In short, the invention is a general method for the direct detection of unlabeled DNA and RNA on a sequence-specific basis.

Moreover, the method can also be used to identify and classify an organism within a phylogenetic group. Thus, the method provides a means for logically dividing organisms into meaningful taxonomic groups based upon the related sequence of their DNA or RNA.

Specifically, a first embodiment of the invention is directed to a method of identifying or classifying organisms on a species-specific or taxon-specific level. The method comprises first providing a surface plasmon resonance-capable substrate having immobilized thereon one or more species- or taxon-specific nucleic acid probes. The substrate is then contacted with a sample known to, or suspected of, containing target nucleic acids from an organism to be identified or classified, under conditions and for a time sufficient for sequence-specific hybridization to occur between target nucleic acids present in the sample and the nucleic acid probes immobilized on the substrate. The substrate is then analyzed by surface plasmon resonance, whereby sequence-specific hybridization between the target nucleic acids present in the sample and the nucleic acid probes immobilized on the substrate is detected. The change in percent reflectivity of the substrate can also be quantified to thereby deduce the concentration and source of the target nucleic acid in the sample tested.

A second embodiment of the invention is directed to a method of analyzing expression of a gene of interest. Here, the method comprises providing a surface plasmon resonance-capable substrate having immobilized thereon one or more nucleic acid probes specifically reactive with mRNA or cDNA corresponding to the gene of interest. The substrate is then contacted with a sample known to, or suspected of, containing mRNA or cDNA corresponding to the gene of interest, under conditions and for a time sufficient for sequence-specific hybridization to occur between the mRNA or cDNA present in the sample and the nucleic acid probes immobilized on the substrate. The substrate is then analyzed by surface plasmon resonance, whereby sequence-specific hybridization between mRNA or cDNA present in the sample and the nucleic acid probes immobilized on the substrate is detected.

A third embodiment of the invention is drawn to a method of detecting and quantifying sequence-specific hybridization of nucleic acids. The method comprises the following steps:

(a) depositing an ω-modified alkanethiol monolayer on a metal substrate;

(b) reacting hydrophobic protecting groups with the monolayer;

(c) patterning the monolayer to create an array of exposed metal substrate areas;

(d) depositing ω-modified alkanethiol in the areas of exposed metal substrate, thereby yielding an array of discrete, unprotected ω-modified alkanethiol spots;

(e) attaching nucleic acid probes to the discrete, unprotected ω-modified alkanethiol spots, thereby yielding an array of discrete spots having nucleic acid probes immobilized thereon;

(f) removing the protecting groups of step (b); and (g) making the monolayer resistant to non-specific protein binding; and then (h) contacting the substrate of step (g) with a sample known to, or suspected of, containing target nucleic acids, under conditions and for a time sufficient for sequence-specific hybridization to occur between target nucleic acids present in the sample and the nucleic acid probes immobilized on the substrate; and then (i) analyzing the substrate by surface plasmon resonance, whereby sequence-specific hybridization between the target nucleic acids present in the sample and the nucleic acid probes immobilized on the substrate is detected.

The primary advantage of the present invention is that the method can be used to probe many nucleic acid samples, including RNA samples, in a very short amount of time, without requiring any labeling of the target or probe nucleic acid, using a recyclable substrate that can be used at least 50 times without signal degradation. The subject SPR-based method offers the simplicity of direct isolation and hybridization of nucleic acid samples to species-specific and/or taxon-specific nucleic acid probes.

The method is highly automatable and can be implemented using high-throughput laboratory robots.

Another advantage of the present invention is that the SPR arrays described herein are fabricated using chemistries that yield very, very robust arrays. In fact, the SPR nucleic acid arrays described herein can be recycled fifty (50) or more times without signal degradation. All that is required to "erase" an earlier hybridization experiment from the substrate is to wash the substrate with 8 M urea. The washing removes any nucleic acids hybridized to the array without removing any of the immobilized nucleic acid probes that define the array itself.

These and other advantages of the subject invention will become clear upon a complete reading of the Detailed Description, Claims, and Drawings that follow.

BRIEF DESCRIPTION OF THE DRAWINGS

FIGS. 2A, 2B, 2C, and 2D show the results for the experiments described in Examples 2 and 3. FIG. 2A is a SPR image of a DNA array hybridized to total cellular RNA from *E. coli*. FIG. 2B is a SPR image of a DNA array hybridized to total cellular RNA from *B. subtilis*. FIG. 2C is a SPR image of a DNA array hybridized to in vitro transcribed rRNA from *E. coli*. FIG. 2D is a SPR image of a DNA array hybridized to in vitro transcribed rRNA from *B. subtilis*.

FIG. 3A is a map of the array elements, showing the positions of DNA Probe A and DNA Probe B within a 4×4 unit cell. FIG. 3B is a SPR image of a 2×2 array of the unit cell shown in FIG. 3A hybridized to DNA complement A'. FIG. 3C is a SPR image of a 2×2 array of the unit cell shown in FIG. 3A hybridized to DNA complement B'. FIG. 3D is plot showing the change in percent reflectivity in the arrays shown in FIGS. 3B and 3C (taken through the dotted line shown in FIGS. 3B and 3C).

DETAILED DESCRIPTION OF THE INVENTION

Abbreviations and Commercial Suppliers

Figure 1:
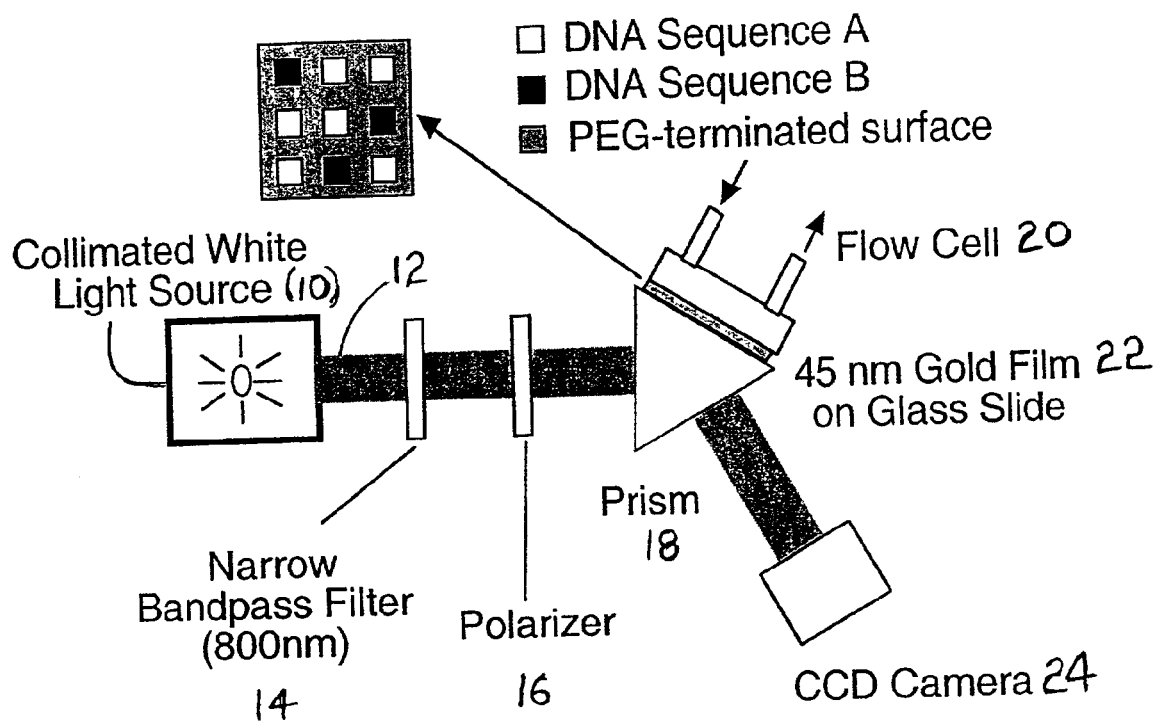
FIG. 1 is a schematic representation of a SPR apparatus that can be utilized in the present invention.

The following abbreviations and terms are used throughout the specification and claims. All other terms have their standard, accepted meaning in the relevant art.

"biomolecule"=any molecule found in biological material, expressly including, but not limited to nucleic acids, proteins, peptides, antibodies, enzymes, cell-wall components such as phospholipids, etc., and modified and synthetic forms thereof, such as labeled biomolecules and recombinant biomolecules.

"BSA"=bovine serum albumin (Sigma Chemical, St. Louis, Mo.).

"DMF"=dimethylformamide.

"Fmoc-NHS"=9-fluorenylmethoxycarbonyl-N-hydroxysuccinimide (Novabiochem, La Jolla, Calif.).

"metal substrate" or "metal film"=a metal thin film of gold, silver, copper, platinum, palladium, rhodium, titanium, and the like. Gold is preferred.

"MUAM"=11-mercaptoundecylamine.

"NHSS"=N-hydroxysulfosuccinimide ester.

"nucleic acids"=deoxyribonucleic acids (DNA), ribonucleic acids (RNA), and peptide nucleic acids from any source, and modified forms thereof, including, without limitation, labeled (radioactive, fluorescent, etc.) nucleic acids, and nucleic acids modified to include a binding moiety such as a thiol group or a biotin tag.

"PEG"=poly(ethylene glycol).

"PEG-NHS"=N-hydroxysuccinimidyl ester of methoxypoly(ethylene glycol) propionic acid MW 2000 (Shearwater Polymers, Inc., Huntsville, Ala.).

"poly(ethylene glycol)-modified alkanethiol"$HS(CH_2)_{11}(OCH_2CH_2)_3OH$.

"SSB"=single-stranded DNA binding protein (Pharmacia Biotech, Piscataway, N.J.).

"SSMCC"=sulfosuccinimidyl 4-(N-maleimidomethyl) cyclohexane-1-carboxylate (Pierce Chemical, Rockford, Ill.).

"TAEA"=tris(2-aminoethyl)amine (Aldrich Chemical, Milwaukee, Wis.).

"TEA"=triethanolamine hydrochloride (Sigma)

"ω-modified alkanethiol"=an alkanethiol whose terminal carbon atom has been modified by the addition of a chemically-reactive moiety such as an amino, hydroxy, carboxy, or thiol moiety.

The above chemicals and were all used as received. Solvents were of standard laboratory grade and Millipore (Marlborough, Mass.) filtered water was used for all aqueous solutions and rinsing.

The chemical modification of a metal substrate to create a surface plasmon resonance-capable nucleic acid array thereon proceeds as described in U.S. Pat. No. 6,127,129, issued 3 Oct. 2000, and incorporated herein by reference. Briefly, these steps proceed as follows:

(1). Self-assembly of an ω-modified alkanethiol monolayer on a metal substrate. The ω-modification to the alkanethiol may be the addition of any moiety with enables further covalent linkages to be made the ω-terminus of the alkanethiol. Such modifications include, without limitation, the addition of an amine group, a hydroxyl group, a carboxyl group, or a thiol group to the ω carbon of the alkanethiol chain. The alkanethiol monolayer is preferably an amino-$C_8$–$C_{24}$-alkanethiol, a straight-chain alkane being much preferred to branched alkane; the most preferred ω-modified alkanethiol is MUAM.

(2). Reaction of the ω-modified alkanethiol surface with a hydrophobic protecting group, most preferably Fmoc.

(3). Photopatterning of the surface to create an array of bare metal areas.

(4). Re-assembly using additional ω-modified alkanethiol to fill in the bare metal array elements, thereby yielding islands of ω-modified alkanethiol.

(5). Covalently attaching biomolecules or cells to the islands of ω-modified alkanethiol.

(6). Removal of the protecting group from the array background.

(7). Reaction of the background with a material, preferably PEG, to make the background resistant to non-specific protein binding.

To ensure the quality of the finished product, each of the above steps may be monitored using PM-FTIRRAS, contact angle measurements, and scanning-angle SPR.

The above steps are now described in greater detail:

Step (1). In step (1), a monolayer of ω-modified alkanethiol, preferably an amine-terminated alkanethiol, most preferably MUAM, is self-assembled from an ethanolic solution onto a silanized substrate (glass or other substrate transparent to the wavelengths of radiation to be used in subsequent analysis) coated with a thin noble-metal film. In the preferred embodiment, a film of gold about 450 Å thick is used. The thickness of the metal film is not overly critical insofar as the film is uniformly applied and will function in SPR imaging analysis. Self-assembled monolayers of ω-modified alkanethiols on gold have been described previously, see, for example, Thomas et al. (1995), and are generally accepted by most to form well-ordered, monomolecular films. However, if left exposed for extended periods of time, the terminal amine groups of amino-modified alkanthiols will react with $CO_2$ to form carbamate salts on the surface. Consequently, amino-terminated alkanethiol-coated substrates should be handled with care and their exposure to $CO_2$ minimized.

Step (2). In step (2) of the array fabrication, the MUAM covered surface is reacted with a reversible protecting group to create a hydrophobic surface. In the case of MUAM, an amine-modified alkanethiol, the protecting group is, appropriately, an amino protecting group, preferably Fmoc. Fmoc is a bulky, hydrophobic, base labile, amine protecting group routinely used in the solid phase synthesis of peptides.

The choice of protecting group used is dependent in large measure upon the nature of the ω-modification made to the alkanethiol. If the ω-modification is the addition of a carboxyl group, a hydrophobic carboxy protecting group would be used. Likewise, if the ω-modification is the addition of a hydroxyl or thiol group, a hydrophobic hydroxy or thiol protecting group, respectively, would be used. Any type of hydrophobic protecting suitable for protecting the ω-modification used on the alkanethiol can be utilized in the present invention. Numerous such protecting groups, for any number of reactive moieties, such as amine, hydroxy, and carboxy functionalities, are known to the art. For example, chloride derivatives of both Fmoc and trityl to can be used to reversibly modify hydroxyl-terminated alkanethiols.

When using Fmoc, the N-hydroxysuccinimide ester of Fmoc (Fmoc-NHS) reacts with the terminal amine moiety of the MUAM molecule to form a stable carbamate (urethane) linkage, covalently attaching the Fmoc group to the surface. After reaction with Fmoc-NHS, the surface properties of the array are changed significantly; the surface is extremely hydrophobic as confirmed by the measured contact angle of 74.4°±2.5°. In addition, an increase in the film thickness to 22.8 Å±0.5 Å is measured with scanning angle SPR.

Step (3). In step (3) the bond anchoring the ω-modified alkanethiol to the metal substrate is selectively cleaved to yield a patterned surface of exposed metal. UV photopatterning is preferred to create the patterned surface, although the means to create the patterned surface is not critical so long as the method reliable yields the desired pattern. For example, micro-contact printing methods can also be used to yield a patterned surface. Using UV patterning, the surface is exposed through a quartz mask to UV radiation which photo-oxidizes the gold-sulfur bond that anchors the alkanethiol monolayers to the surface. The surface is then rinsed, removing the photo-oxidized alkanethiol and leaving an array of bare metal pads surrounded by a hydrophobic MUAM+Fmoc background.

Step (4). In step (4), the surface is again exposed to an ω-modified alkanethiol solution (in the preferred embodiment an ethanolic solution of MUAM) whereby the alkanethiol assembles into the bare gold regions producing a surface composed of hydrophilic MUAM pads surrounded by the hydrophobic Fmoc background. This difference in hydrophobicity between the reactive MUAM regions and the background is essential for the pinning of small volumes of aqueous biomolecule or cell solutions onto individual array locations.

Step (5). In step (5) in the process, biomolecules or cells (preferably nucleic acids, and more preferably still, DNA) are then covalently attached to the surface. The MUAM reactive pads are first exposed to a solution of a bifunctional linker. The linker must be capable of binding at one end to the ω-modified alkanethiol surface and at the other end to the biomolecule or cell to be immobilized to form the desired array. Any bifunctional linker having these characteristics can be used in the present invention. The preferred bifunctional linker is SSMCC, a heterobifunctional linker which contains both an N-hydroxysulfosuccinimide (NHSS) ester and a maleimide functionality. The NHSS ester end of the molecule reacts with the free amine groups on an amino-modified surface, such as the MUAM spots, creating pads terminated in maleimide groups which are reactive towards thiol. Small volumes (0.08 to 0.1 L) of 1 mM solutions of 5'-thiol-modified DNA sequences are then spotted at discrete array locations and react to form a covalent attachment to the surface, Using this technique, a whole host of biomolecules (DNA, RNA, proteins, lipids, etc.) and/or whole cells can be spotted at different array locations.

A variation on this attachment scheme whereby thiol-DNA is linked via SSMCC to a MUA/PL (11-mercaptoundecanoic acid/poly-L-lysine) bilayer has been used quite extensively, see U.S. Pat. No. 5,629,213. Other researchers have used the direct self-assembly of thiol-terminated DNA molecules on gold to prepare functionalized surfaces, but this method has the disadvantage that only weak forces exist for the self-assembly of oligonucleotide molecules and hence, the DNA can also non-specifically adsorb to the bare gold surface.

In the preferred approach, a bifunctional linker is used to attach 5'-thiol-modified oligonucleotide sequences to reactive pads of aminoalkanethiol. The bifunctional linker preferably contains a functionality reactive towards amines and a functionality reactive towards aminoalkanethiols. The surface is first exposed to a solution of the linker, whereby one end of the molecule reacts with the aminoalkanethiol surface. Excess linker is rinsed away and the array surface is then spotted with 5'-thiol-modified nucleic acid which reacts with the other end of the bifunctional linker, forming a covalent bond between the nucleic acid and the surface monolayer.

Step (6). In step 6 the protecting group (Fmoc) is removed from the array surface. Preferably, this is accomplished by exposure to a 1M solution of the secondary amine, TAEA, in DMF. Many basic secondary amines can be used to remove Fmoc from the surface; for example, 1 M solutions of ethanolamine and piperidine can be used with equal success. TAEA was chosen specifically as the deprotection agent since it effectively scavenges the dibenzofulvene byproduct and is efficiently rinsed from the array surface. After this deprotection step, the array background has been converted back to the original ω-modified alkanethiol surface.

Step (7). In the final step of the array fabrication, the ω-modified alkanethiol background is reacted with a compound to create a background that is resistant to the non-specific binding of proteins. The preferred compound for this purpose is PEG-NHS, although any compound which will selectively bind to the ω-modified alkanethiol surface and inhibit non-selective protein binding can be used. In order to monitor the binding of proteins to arrays of surface-bound biomolecules or cells, it is critical that the array background prohibit the non-specific adsorption of protein molecules. Significant amounts of such non-specific binding obscures the measurement of small amounts of protein binding at specific array locations.

To create a background that is resistant to the non-specific binding of proteins, the MUAM surface was reacted with PEG-NHS. As was the case in the Fmoc-NHS+MUAM reaction, PEG-NHS reacts with the terminal amine groups of the MUAM to form an amide linkage, covalently attaching the PEG polymer chain to the surface. The preferred PEG-NHS polymer has an average molecular weight of 2000 and contains one NHS ester moiety per molecule, allowing for a single point of attachment. After the reaction of the deprotected surface with PEG-NHS, the surface remains hydrophilic and has a measured contact angle of $37.3°+2.6°$. A total thickness of 23.8 Å±0.8 Å was measured for a MUAM monolayer film after reaction with PEG-NHS. This increase of only 6 Å of PEG suggests that only a small fraction of the amine groups of the MUAM are modified and that the oligo(ethylene glycol) chains are lying flat across the surface.

Referring now to FIG. 1, depicted in the figure is a schematic of a Near IR-SPR imager instrument and the surface chemistry used in the present invention. Collimated white light 12 generated by a collimated white light source 10 passes first through a narrow bandpass filter 14 (800 nm), a polarizer 16, and a glass prism 18. A glass slide with a thin (45 nm) coating of gold 22 is optically coupled to the prism 18. The surface of the gold film is chemically modified with a nucleic acid array as depicted in FIG. 1. Methoxypoly (ethylene glycol) propionic acid (PEG) groups surround the DNA spots and prevent non-specific adsorption onto the background of the array. Light at 800 nm interacts with the patterned DNA array on gold from behind, creating surface plasmons. The array is imaged in the presence of hybridization buffer. A nucleic acid target sample, for example, an RNA target sample, is introduced using a flow cell 20. Changes in the index of refraction at nucleic acid spots where hybridization adsorption of target nucleic acid occurs affects the percent reflectivity of the incident light. These changes in percent reflectivity are detected with a CCD camera 24. The signals captured by the CCD can be integrated or otherwise manipulated by means of a programmable computer to generate output in the form of images or data. The signals captured by the CCD can also be mathematically manipulated, for example, to compare the changes in percent reflectivity to calculate the concentration of the target nucleic acid in the sample tested, etc.

In practice the subject method proceeds in a very straightforward fashion, and is guided in large measure by the question being probed by the investigator. For example, the first embodiment of the invention is directed to a method of identifying or classifying organisms on a species-specific or taxon-specific level. Thus, the first step in the method is to provide or otherwise fabricate a SPR-capable substrate having immobilized thereon one or more species- or taxon-specific nucleic acid probes. The substrate is preferably prepared as detailed in steps 1–7, above. It must be noted, however, that while the above method is preferred, so long as the method of fabrication results in an SPR-capable substrate having immobilized thereon one or more probe nucleic acids, the fabrication method is not overly critical to the functionality of the method.

In view of the fact that the entire genomes of several organisms have been sequenced and are readily available in publicly-accessible computer databases, selecting a species- or taxon-specific probe is simply a matter of comparing various known sequences within the species or taxon to be targeted and comparing the homology of the chosen sequences to those in other organisms outside the chosen species or taxon. Literally millions of other sequences from an equally large number of organisms are cataloged on-line and available to the public from such sources as GenBank, as well as for-profit commercial suppliers. As described in the Examples, ribosomal RNA (rRNA) provides many sequences that can be used to target and to distinguish between specific organisms. (The Examples include an experiment that shows that the present invention can clearly distinguish between *E. coli* rRNA and *B. subtilis* rRNA.)

The SPR substrate with the nucleic acid probes immobilized thereon is then contacted with a sample known to, or suspected of, containing target nucleic acids from an organism to be identified or classified. The sample itself can be isolated from an nucleic acid source without limitation, including animal, plant, fungi, algae, eukaryote, prokaryote, single-celled organisms, multi-cellular organisms and higher-level organisms, such as mammals. The sample can be prepared by any method or means now known to the art or developed in the future that is capable of rendering the nucleic acid within the sample available for hybridization reactions. A number of such means are known to the art (see the Examples). The sample may contain DNA, RNA, or both DNA and RNA. In short, the source of the nucleic acid to be tested is not critical to the invention, nor is the means by which the nucleic acid is isolated from the source (so long as the isolation means renders nucleic acid capable of undergoing hybridization). When using total cellular RNA as a sample, it is generally preferred that the RNA be fragmented prior to analysis to reduce the secondary structure found in the RNA. This can be done by applying high pressure to the RNA sample or boiling the sample in an appropriate solution (such as an aqueous solution of $Mg^{2+}$), as discussed in the Examples. The nucleic acid within the sample to be tested need not be "pure" in the sense that other, non-nucleic acid, entities (proteins, phospholipids, cell fragments, etc.) may be present in the sample without adversely affecting the method. The sample may also be denatured by boiling in a standard buffer for 5 to 10 minutes. This reduces the secondary structure of the RNA molecules without fragmentation.

The sample is contacted with the SPR substrate under conditions and for a time sufficient for sequence-specific hybridization to occur between target nucleic acids present in the sample and the nucleic acid probes immobilized on the substrate. See the Examples for a more detailed discussion of the times and buffers. Generally, the time required for good results is determined empirically by running the experiment in series, and altering the exposure time systematically. If the exposure time is too short, the nucleic acids present in the will not have enough time to hybridize to the complementary, immobilized probes. If the exposure time is too long, non-specific hybridization may occur.

After exposure, the substrate is rinsed and then analyzed by surface plasmon resonance. It is preferred that the sample be analyzed by SPR imaging, to thereby generate a image of the array. The change in percent reflectivity of the substrate can also be quantified to thereby deduce the concentration and nature of the target nucleic acid in the sample tested.

The second embodiment of the invention, drawn to a method of analyzing expression of a gene of interest, proceeds in the same fashion as the first, with the exception that the immobilized probes are selected based on different criteria. Here, a gene of interest is generally known and its expression is to be investigated (e.g., the timing of gene expression, the amount of gene expression, the location of gene expression, etc.). In this embodiment, the method comprises providing a surface plasmon resonance-capable substrate having immobilized thereon one or more nucleic acid probes specifically reactive with mRNA or cDNA corresponding to the gene of interest. The substrate is then contacted with a sample known to, or suspected of, containing mRNA or cDNA corresponding to the gene of interest, under conditions and for a time sufficient for sequence-specific hybridization to occur between the mRNA or cDNA present in the sample and the nucleic acid probes immobilized on the substrate.

In this embodiment, samples can be prepared from a series of cells, for example, in early log-phase growth, late log-phase growth, in stasis, etc. Such an approach would be used to evaluate the expression of a given gene as a function of cellular growth phase—dividing versus static.

Samples could also be prepared from a given colony after fragmenting the cells and isolating the sub-cellular components. This approach would be used to evaluate expression based upon location within the cell (e.g., nucleus, cytoplasm, peroxisome, etc.). Of course, gene expression could be analyzed based on cell type in higher organisms, e.g., liver vs. kidney vs. neuron, etc.

The substrate is then analyzed by surface plasmon resonance, as noted herein.

A third embodiment of the invention is drawn more generally to a method of detecting and quantifying sequence-specific hybridization of nucleic acids. This embodiment proceeds in exactly the same fashion as noted above, using probes specific for the nucleic acid of interest. In the most preferred third embodiment, the method utilizes steps 1–7 above to fabricate the SPR substrate. The analysis then proceeds as in the other embodiments.

Increasing solution stringency and high temperature washing buffers can improve specificity. Additionally, the quality of the results, or, more specifically, the quality of the inferences that can be drawn from the results of any given experiment utilizing the present method, can be improved by using more than a single probe for each target of interest (gene, organism, etc.) on the SPR array. As in any scientific experiment, while a conclusive determination of a given hypothesis can be predicated upon a single data point, prudence dictates that a single probe should not be relied upon to make conclusive determinations about the presence of a particular DNA or RNA molecule within a sample tested. Thus, in the preferred embodiment, the SPR substrate has immobilized thereon more than one area of probe nucleic acid and/or more than one type of probe nucleic acid. This, however, does not exclude from the scope of the invention using an SPR substrate having immobilized thereon a single, monolithic, homogeneous layer of the same type of probe nucleic acid.

Array elements can be individually spotted using as little as 40 nL of target sample solution. This permits the label-free detection of as little as 2 femtomole of DNA per array spot. When the rRNA detection limit determined here is considered, that translates to 0.1 ng RNA per spot, or RNA from ~5000 metabolically-active cells.

A major advantage of SPR imaging as opposed to conventional SPR angle techniques is its ability to create built-in controls within the array itself to distinguish between specific and non-specific surface interactions. For example, the amount of DNA mismatch in an experiment such as that described in Examples 5 and 6 (see below) can be used to monitor and quantify non-specific interactions. With this ability in hand, reaction parameters can easily be optimize to maximize the specificity of the hybridization. For instance, in Example 5, even at high concentrations of complement target DNA, non-specific binding is negligible.

The stringency of the hybridization reaction is affected by a number of parameters, the most notable being temperature, salt concentration, pH, and the presence of denaturants such as urea or formamide. For Example 5, a reaction solution of 300 mM NaCl, 20 mM phosphate buffer at pH 7.0, 20 mM EDTA, and 100 mM urea resulted in the highest amount of hybridization without sacrificing specificity. Starting from this set of parameters, increasing the salt concentration resulted in more target DNA adsorption to both the matched and mismatched spots (i.e., both specific and non-specific adsorption increased). Decreasing the salt concentration below 200 mM resulted in less hybridization to the perfect match. Suffice to say, where high discrimination is required (as when probing for closely related sequences), more stringent conditions may be necessary. One of skill in the art is capable of systematically varying one parameter at a time to arrive at an optimum set of reaction conditions (temperature, salt concentration, pH, and presence of denaturants) for any given analysis.

EXAMPLES

The following Examples are included solely to provide a more complete understanding of the present invention. The Examples do not limit the scope of the invention disclosed and claimed herein in any fashion.

Standard Procedures

Reagents: All chemicals were obtained from Sigma Chemical Co. (St. Louis, Mo.), unless otherwise indicated. Gold substrates used in contact angle measurements were purchased commercially (Evaporated Metal Films) and those used in scanning or imaging SPR measurements were prepared by vapor deposition onto microscope slide covers that had been silanized with (3-mercaptopropyl)-trimethoxysilane (Aldrich) in a manner similar to that reported by Goss et al. (1991) Anal. Chem. 63:85–88.

All oligonucleotides were synthesized on an ABI (Foster, Calif.) DNA synthesizer at the University of Wisconsin Biotechnology Center. Oligonucleotides included a 5' thiol modifier C6 as well as a 15-T spacer prior to the rRNA complementary sequence to provide additional spacing away from the gold surface. GlenResearch's (Sterling, Virginia) "5'-Thiol-Modifier C6" and ABI's "6-FAM" were used for 5'-thiol-modified and 5'-fluorescein-modified oligonucleotides respectively, and "Spacer Phosphoramidite 18" (Glen Research) was used for the addition of an ethylene glycol spacer region. Thiol-modified oligonucleotides were deprotected as outlined by Glen Research's product literature.(Glen Research Corp. (1990) "User Guide to DNA Modification and Labeling"). Before use, each oligonucleotide was purified by reverse-phase binary gradient elution HPLC (Shimadzu (Columbia, Md.) "SCL-10AVP") and DNA concentrations were verified with an HP8452A UV-VIS spectrophotometer (Hewlett-Packard, Palo Alto, Calif.).

SPR Imaging Apparatus: The in situ SPR imaging instrument is a modified version of that described previously, (Jordan & Corn 1997; Thiel et al. 1997; Jordan et al. 1997; and Frutos et al. 1998), in which the HeNe laser and beam expander have been replaced by a collimated white light source/bandpass filter combination. A more thorough discussion of this modification in the context of near IR (NIR) SPR imaging is reported elsewhere, see Nelson et al. (1999). In short, a collimated, polychromatic beam of light was used to illuminate an SF10 prism/Au/thin film/buffer assembly at a fixed incident angle near the SPR angle. The reflected light was passed through a 10 nm bandpass filter (830 nm) and was collected with an inexpensive CCD camera. Differences in the reflected light intensity measured at various locations on the sample create the image and are a direct result of differences in the thickness or refractive index of the material bound at the gold surface. Data work-up was done using NIH Image v. 1.61 software.

Multi-step array fabrication: A clean gold substrate was immersed in a 1 mM ethanolic solution of MUAM for at least one hour to allow for the adsorption and self-assembly of the aminoalkanethiol monolayer. The substrate was rinsed with ethanol and water, dried under a stream of $N_2$, and was then reacted with a solution of Fmoc-NHS (3 mM in 1:1 DMSO: 100 mM TEA buffer, pH 7). The sample was soaked briefly in DMSO to remove unreacted Fmoc-NHS from the surface and then photopatterned by irradiating the sample with UV light from a mercury-xenon arc lamp through a quartz mask. Subsequent rinsing of the sample with ethanol and water removed alkanethiol from the exposed areas. The sample was re-exposed to the ethanolic MUAM solution resulting in an array of MUAM elements surrounded by a hydrophobic MUAM+Fmoc background. Single-stranded, 5'-thiol modified DNA was then immobilized onto the array locations using an attachment scheme modified slightly from that used previously.

Briefly, the amine-terminated MUJAM array elements were spotted with 0.1 $\mu$L of a 1 mM solution (in 100 mM TEA, pH 7) of the heterobifunctional linker SSMCC, creating a thiol-reactive, maleimide-terminated surface. 5'-Thiol-modified DNA sequences were then covalently attached to these maleimide-terminated array elements by spotting the sample with 0.1 $\mu$L drops of solutions containing 1 mM DNA onto the specific array locations and reacting for at least 2 hours in a humid environment to prevent solvent evaporation. After exposure to the DNA solution, the surface was rinsed with water and soaked in buffer to remove unbound DNA sequences. The Fmoc was then removed from the background by immersing the array in a 1 M solution of TAEA in DMF for 10 minutes. The deprotected surface was rinsed with water and subsequently reacted with 4 mM PEG-NHS (in 100 mM TEA, pH 8) to pegylate the array background, rendering it resistant to protein non-specific binding.

Total cellular RNA preparation: E. coli strain DH10B (Gibco-BRL, Rockville, Md.) and B. subtilis strain 168 (ATCC 23857, American Type Culture Collection, Manassas, Va.) were grown at 37° C. overnight with aeration in 2 mL of Luria-Bertani (LB) broth. The next morning, 100 mL fresh LB medium was inoculated at a 1:100 dilution with the overnight-grown cultures, and grown at 37° C. until the cultures reached mid-log phase growth ($A_{600}$=0.7). Total cellular RNA was routinely extracted from 10 mL of cell culture using an "RNeasy" midi kit (Qiagen, Valencia, Calif.), following the manufacturer's protocol. RNA yield and quality was assessed by agarose gel electrophoresis, followed by ethidium bromide staining.

In vitro rRNA preparation: The 16S rRNA genes from E. coli and B. subtilis were PCR amplified from genomic DNA using the bacteria-specific primers 27F (5'-AGAGTTTGATC(AIC)TGGCTCAG-3') (SEQ. ID. NO: 1) and 1492R (5'-GG(C/T)TACCTTGTT-ACGACTT-3') (SEQ. ID. NO: 2), and the resulting PCR products cloned into the pGEM-T Easy vector (Promega Corp., Madison, Wis.). In vitro 16S rRNA transcripts from E. coli and B. subtilis, respectively, were made using the "Ribomax" in vitro transcription system (Promega). Briefly, the cloned rRNA genes were linearized using an enzyme generating a 5' overhang, and then in vitro transcribed according to the manufacturer's protocol. Template DNA was removed using "RQ1" RNAse-free DNAse (Promega), followed by phenol-chloroform extraction.

Ribosome preparation: E. coli or B. subtilis were grown in 100 mL LB until the cell cultures reached log-phase growth. The cells were harvested by centrifugation, washed once in a homogenization buffer (20 mM Tris-HCl (pH 7.4), 10.5 magnesium acetate, 100 mM ammonium chloride, 0.5 mM EDTA, and 3 mM β-mercaptoethanol) and then lysed using a French press at 12.66 kg/mm$^2$ (18,000 psi). Cell lysates were subjected to centrifugation at 14,000 rpm in a Beckman microcentrifuge for 30 minutes at 4° C., after which the supernatants containing intact ribosomes were removed. Ribosomes were pelleted by pipetting this supernatant above a 1.1 M sucrose (in homogenization buffer) cushion, and subjecting the samples to centrifugation at 37,500 rpm in a Beckman 70 Ti rotor for 16 hours at 4° C. The ribosomal pellet was carefully washed with 70% ethanol, dried, and then resuspended in RNAse-free water. To remove ribosomal-associated proteins, the samples were first fragmented (see following paragraph), and then treated with 1 mg/mL proteinase K for 4 hours at 37° C., followed by five rounds of phenol-chloroform extraction. RNA yield and size were determined by agarose gel electrophoresis, and the loss of ribosomal-associated proteins was verified by polyacrylamide gel electrophoresis.

RNA fragmentation: To reduce RNA secondary structure in some cases, RNAs were fragmented via incubation in a magnesium fragmentation buffer (40 mM Tris acetate (pH 8.1), 100 mM potassium acetate, and 30 mM magnesium acetate) at 95° C. for 10 minutes. RNA was subsequently ethanol precipitated, rinsed multiple times in DEPC-treated 70% ethanol, and then resuspended in RNAse-free water. The extent of RNA fragmentation was assessed by agarose gel electrophoresis. RNA samples were stored at −20° C.

Example 1

DNA Probe Design rRNA regions to target with DNA probes were selected by aligning the respective E. coli and B. subtilis rRNA sequences, and then identifying regions of dissimilarity. Thus, DNA probes were chosen based both upon optimal species differentiation for a specific rRNA region, and avoiding sequences with any features that could be anticipated to complicate or interfere with the intended hybridization.

By using two bacteria with completely sequenced genomes (i.e., E. coli and B. subtilis), probes predicted to bind to other abundant RNA molecules made by the cells can and were eliminated. Probes of approximately eighteen bases were designed, each with at least an eight-base mismatch required upon alignment of the two species' 16S rRNA gene sequences. Self-hybridization and secondary structure were also a consideration. For example, EUB338, a probe used for whole cell hybridization in situ, Amann (1990), was found to be ineffective at binding 16S rRNA from any species when used as a probe on the subject nucleic acid arrays. By shifting the sequence only a few bases, a predicted self-complementary sequence forming a hairpin was avoided, and the newly designed probe was found to bind successfully to RNA of all microbial species examined (i.e., E. coli, B. subtilis, and B. cereus). The sequence of the redesigned probe, designated EUB342, is listed in Table 1.

universal probe, EUB338, and is designed to bind to the 16S rRNAs of all known bacteria.

To confirm that DNA probes were equally accessible for hybridization, perfectly matched oligonucleotide complements were tested for each probe. These were found to hybridize successfully and specifically.

Example 2

Species-Specific Identification of rRNA Using Total RNA

Referring now to FIGS. 2A and 2B, four probes were fixed to the surface of an SPR substrate: E186 (a probe for E. coli), B491 (a probe for B. subtilis), EUB342 (a "universal" bacterial probe), and the negative control listed in Table 1. Again, probes beginning with an "E" are targeted toward and perfectly complementary to the E. coil 16S rRNA sequence, and those beginning with a "B" are likewise targeted toward and perfectly complementary to the B. subtilis 16S rRNA sequence. DNA probes were spotted onto the array in geometric patterns for easy recognition, as shown in the legend. Hybridization adsorption onto the array is indicated by a change in the percent reflectivity of incident light.

In FIG. 2A, a 35 mg sample of fragmented total RNA from E. coli was first exposed to the array for 1 hour. The resulting change in percent reflectivity upon E. coli hybridization for the probe EUB342 was 2.6%. After this measurement, the array was denatured (i.e., "erased") by washing the array with 8 M urea. The experiment was then repeated using the erased array and with the same amount of fragmented total RNA from B. subtilis. The results are shown in FIG. 2B. As is readily apparent from comparing the pattern of spots in FIGS. 2A and 2B, total RNA from E. coli hybridized only to the E. coli probe spots and the "universal probe" spots (FIG. 2A). Total RNA from B. subtilis hybridized only to the B. subtilis spots and the "universal probe" spots (FIG. 2B).

The results depicted in FIGS. 2A and 2B show that the present invention has utility in identifying organisms based upon the specific reactivity of the organism's nucleic acid.

TABLE 1

Oligonucleotide Sequences for Probe (i.e., Surface-Immobilized) DNA:

| Symbol | Base Position[†] | Sequence | |
|---|---|---|---|
| E186 | 186–205 | 5'-GTCCCCCTCTTTGGTCTTGC-3' | (Seq. Id. No: 3) |
| E434 | 434–449 | 5'-CTCCCCGCTGAAAGTA-3' | (Seq. Id. No: 4) |
| E491 | 491–505 | 5'-CGGTGCTTCTTCTGC-3' | (Seq. Id. No: 5) |
| B186 | 186–206 | 5'-CTTTTATGTTTGAACCATGCG-3' | (Seq. Id. No: 6) |
| B434 | 434–449 | 5'-TTCCCTAACAACAGAG-3' | (Seq. Id. No: 7) |
| B491 | 491–506 | 5'-CGTGGCTTTCTGGTTA-3' | (Seq. Id. No: 8) |
| EUB342 | 342–357 | 5'-ACTGCTGCCTCCCGTAG-3' | (Seq. Id. No: 9) |
| NC | Negative Control | 5'-GGATGTGTGTGGAGTGTTAGAAAG-3' | (Seq. Id. No: 10) |

[†]Positions are relative to the published E. coli 16S rRNA sequence

The probes whose symbols begin with an "E" are complementary to E. coli, and those whose symbols begin with a "B" are taken from B. subtilis. A "universal" bacterial probe, designated "EUB342," is a variation of the more common Specifically, this Example shows that such identification can be accomplished using total RNA as a sample to be tested. This Example also shows that the arrays can be re-used by simply rinsing the array with a solution of urea.

Example 3

Species-Specific Identification of rRNA Using in Vitro Transcribed RNA

In FIG. 2C, a 50 mg sample of in vitro transcribed 16S ribosomal RNA from *E. coli* was first exposed to the array for 1 hour. The resulting change in percent reflectivity upon *E. coli* hybridization for probe EUB342 was 3.9%. After this measurement, the array was erased using 8 M urea. In FIG. 2D, the experiment was then repeated using the erased array and with the same amount of in vitro transcribed 16S ribosomal RNA from *B. subtilis*. To demonstrate the highly reusable nature of the surface chemistry, the array depicted in FIGS. 2C and 2D was hybridized and denatured (erased) more than twenty (20) times before the data shown in FIGS. 2C and 2D were taken.

As is readily apparent from comparing the pattern of spots in FIGS. 2C and 2D, in vitro transcribed rRNA from *E. coli* hybridized only to the *E. coli* probe spots and the "universal probe" spots (FIG. 2C). Transcribed rRNA from *B. subtilis* hybridized only to the *B. subtilis* spots and the "universal probe" spots (FIG. 2D).

Because in vitro transcribed 16S rRNA is free of cellular proteins, DNA, or other forms of RNA, the similarity of these results to those in Example 2 indicates that the common signals observed are due to 16S rRNA, and not from interactions contributed by other cellular components in the sample.

Comments on Examples 1, 2, and 3

Examples 1, 2, and 3 show that the invention can be used to identify the origin of nucleic acid on a species-specific basis using total RNA or in vitro transcripts.

In all of FIGS. 2A, 2B, 2C, and 2D, note the excellent signal to noise for unlabeled RNA detection. Note also that in the results from both *E. coli* and *B. subtilis*, adsorption to the negative control and to the PEG background is virtually undetectable, allowing easy recognition of the RNA hybridization.

The lower limit of detection for fragmented total *E. coli* RNA was found to be approximately 2 mg/mL (i.e., 1 µg of total RNA in 500 µL of injected sample). rRNA isolated using other techniques was also tested in the same fashion as in Examples 2 and 3 to show that the RNA isolation method is not critical to the functionality of the invention. *E. coli* and *B. subtilis* rRNA was isolated by high-pressure (i.e., French press) lysis followed by isolation of intact ribosomes by ultracentrifugation and subsequent rigorous proteinase treatments and phenol/chloroform extractions. Hybridization of these rRNA samples (which included 5S, 16S, and 23S rRNAs) was very similar to those observed for isolations of total RNA as in Example 2 (data not shown). Taken together, these data indicate that rRNA prepared by a variety of methodologies, and in the presence of many other RNA molecules, can be detected in a sequence-specific, species-specific, and/ortaxon-specific manner using SPR imaging on recyclable arrays.

Example 4

Speed of Method

A major advantage of the present invention is the small amount of time required between culturing of the cells and acquiring the needed hybridization data using SPR imaging. This time-saving advantage is demonstrated in this Example.

Total cellular RNA used in this Example was isolated from bacterial cell cultures during logarithmic growth using a simple 30-minute isolation using a standard commercial kit ("RNeasy"-brand, Qiagen, Valencia, Calif.). In the images shown in FIGS. 2A and 2, the total RNA samples were fragmented prior to introduction into the flow cell to alleviate any potential interference due to 16S rRNA secondary structure, Lockhart (1996). However, it has been shown that simply boiling the total RNA sample for 5 minutes prior to introduction into the flow cell gave virtually identical results (data not shown) compared to fragmented RNA. Gel electrophoresis revealed that the 16S rRNA remained intact after boiling.

The import of this discovery is that label-free detection of RNA is possible in as little as 35 minutes from culture to analysis using a standard commercial kit for isolating total RNA, with an additional one hour required for the SPR hybridization measurement itself

Example 5

Sequence-Specific Nucleic Acid Detection and Analysis

SPR imaging can be used for the sequence-specific detection of small, unlabeled DNA molecules at low concentration using hybridization adsorption onto a surface array as described herein. Measurements of DNA hybridization have been performed previously using SPR angle scan techniques, but these measurements required high concentration and/or amplification of the target DNA to achieve a measurable signal. In previously-published measurements of the hybridization of unlabeled DNA, target concentrations are approximately 1 µM. See, for example, Brockman et al. (1999) and Thiel et al. (1997). The present invention, however, takes advantage of near-infrared excitation, which results in a sharper SPR minimum on gold and subsequently greater contrast in SPR imaging.

This Example demonstrates that label-free detection of low concentration target DNA can be accomplished using the present method. Here, two 18-mer oligonucleotide probes were assembled into an SPR array as described hereinabove. The two immobilized probes, designated A and B, and their perfect complements, designated A' and B', had the following sequences:

Probe A: 5'-GCC GAA GCC ACC TTT TAT-3' (SEQ. ID. NO: 11)

Probe A': 5'-ATA AAA GGT GGC TTC GGC-3' (SEQ. ID. NO: 12)

Probe B: 5'-GCC AGC TTA TTC AAC TAG-3' (SEQ. ID. NO: 13)

Probe B' 5'-CTA GTT GAA TAA GCT GGC-3' (SEQ. ID. NO: 14)

Figure 3C:
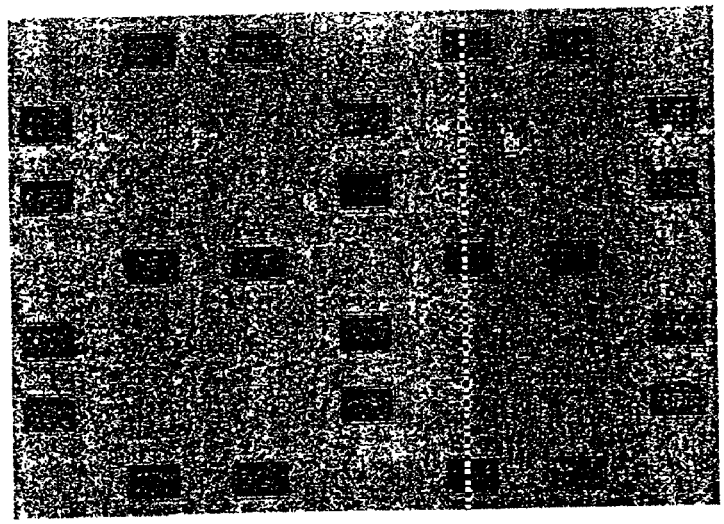
FIGS. 3A, 3B, 3C, and 3D show the results for the experiments described in Examples 5 and 6.
Figure 3B:
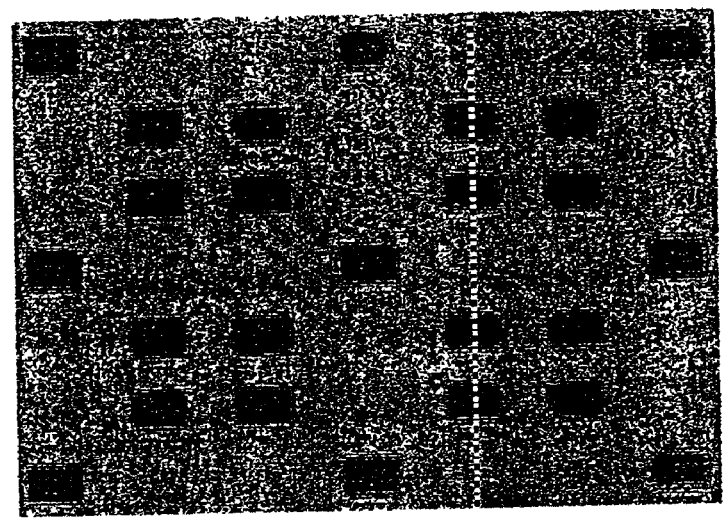
Figure 3A:
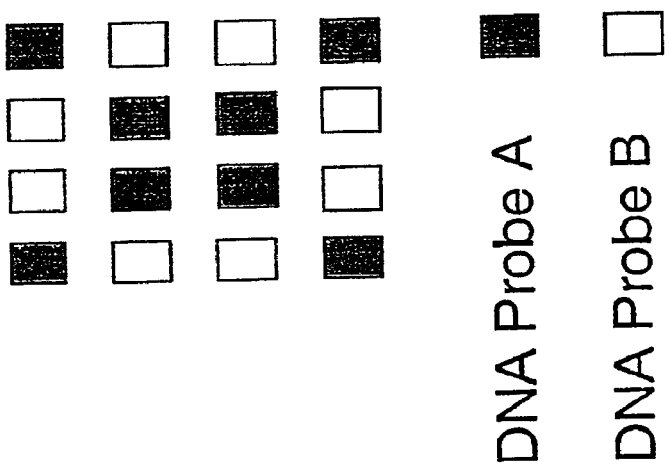
Figure 3D:
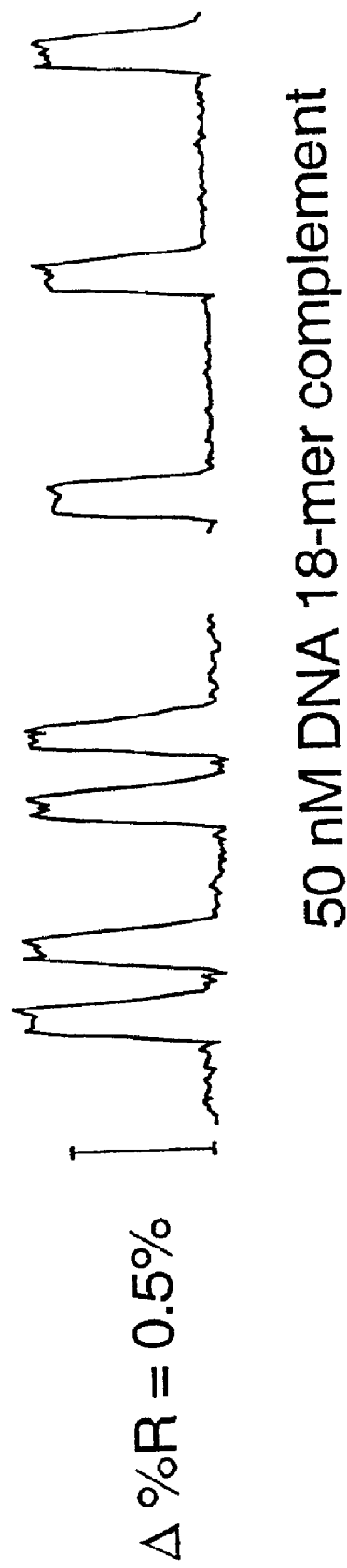

Probes A and B were immobilized to a SPR substrate as described herein in a distinctive pattern of spots as illustrated in FIG. 3A. The 4×4 pattern was repeated 4 times on the substrate, thereby yielding a substrate having a 8×8 pattern (see FIGS. 3B and 3C). In FIG. 3B is shown the SPR array after the array was exposed to a 50 nM solution of DNA complement A' for 30 minutes. As is clear from the pattern seen in FIG. 3B, when exposed to DNA complement A', hybridization occurred preferentially at only those spots where Probe A was immobilized to the substrate.

The substrate was then washed with 8 M urea and exposed to a 50 nM solution of DNA complement B' for 30 minutes. As is clear from the pattern seen in FIG. 3C, when exposed to DNA complement B', hybridization occurred preferentially at only those spots where Probe B was immobilized to the substrate.

The array shown in FIGS. 3B and 3C was denatured and hybridized 25 times without any lose of signal clarity or degradation in the signal-to-noise ratio.

This Example shows that the presently disclosed method can be used to detect and analyze nucleic acids in a sequence-specific fashion using SPR. This Example also demonstrates that the SPR substrates are recyclable.

Example 6

Quantitative Analysis

The arrays depicted in FIGS. 3B and 3C can be used to generate quantitative information regarding the binding onto each spot in the array. This is done by integrating the values of percent reflectivity across a linear or rectangular region of the array (or, for that matter, any user-defined region of the array). In this Example, a line profile taken across the fifth row of the array, as shown by the dotted line in FIGS. 3B and 3C shows quantitatively the change in percent reflectivity for both hybridization events. These plot profiles can be correlated with changes in percent reflectivity. In FIGS. 3B and 3C, hybridization from a 50 nM solution of target DNA resulted in a ~0.6% change in the percent reflectivity. Concentrations of DNA as low as 10 nM were easily detected using the array of Example 5.

The number of molecules required to make a ~0.6% change in the percent reflectivity can be calculated from a separate fluorescence wash-off experiment. Here, fluorescently-labeled target DNA is hybridized onto a surface array from a 50 nM DNA solution and the array is denatured. The denatured DNA from the array is then quantified using the fluorescent label. This experiment has been conducted with the array of Example 5, and the density of target DNA hybridized on the surface was found to be $\sim 1 \times 10^{12}$ molecules/cm$^2$ (using a target DNA concentration of 50 nM). This corresponds to 4 fmol of material adsorbed on to each 500×500 $\mu$m spot.

What is claimed is:

1. A method of identifying or classifying organisms on a species-specific or taxon-specific level comprising:
   (a) providing a surface plasmon resonance-capable substrate having immobilized thereon one or more species- or taxon-specific nucleic acid probes; then
   (b) contacting the substrate with a sample known to, or suspected of, containing target nucleic acids from an organism to be identified or classified, under conditions and for a time sufficient for sequence-specific hybridization to occur between target nucleic acids present in the sample and the nucleic acid probes immobilized on the substrate, wherein the nucleic acids present in the sample are fragmented before contacting the substrate to the sample; and then
   (c) analyzing the substrate by surface plasmon resonance, whereby sequence-specific hybridization between the target nucleic acids present in the sample and the nucleic acid probes immobilized on the substrate is detected; and then
   (d) identifying or classifying the organism from step (b) based upon the specific hybridization detected in step (c).

2. The method of claim 1, wherein in step (a) is provided a substrate having a plurality of DNA probes arranged in an array.

3. The method of claim 1, wherein in step (a) is provided a substrate having a plurality of RNA probes arranged in an array.

4. The method of claim 1, wherein in step (b), the substrate is contacted with a sample containing DNA.

5. The method of claim 1, wherein in step (b), the substrate is contacted with a sample containing RNA.

6. The method of claim 1, wherein in step (b), the substrate is contacted with a sample containing ribosomal RNA.

7. The method of claim 1, wherein in step (c) the substrate is analyzed by surface plasmon resonance imaging.

8. The method of claim 1, wherein the nucleic acids present in the sample are fragmented by applying sufficient pressure to the sample to cause nucleic acid fragmentation.

9. The method of claim 1, wherein the nucleic acids present in the sample are fragmented by heating the sample to a sufficient temperature and for a sufficient amount of time to cause nucleic acid fragmentation.

10. A method of analyzing expression of a gene of interest comprising:
   (a) providing a surface plasmon resonance-capable substrate having immobilized thereon one or more nucleic acid probes specifically reactive with mRNA or cDNA corresponding to a gene of interest; then
   (b) contacting the substrate with a sample known to, or suspected of, containing mRNA or cDNA corresponding to the gene of interest, under conditions and for a time sufficient for sequence-specific hybridization to occur between the mRNA or cDNA present in the sample and the nucleic acid probes immobilized on the substrate; and then
   (c) analyzing the substrate by surface plasmon resonance, to detect sequence-specific hybridization between mRNA or cDNA present in the sample and the nucleic acid probes immobilized on the substrate; and then
   (d) determining timing of expression of the gene of interest, amount of the gene of interest expressed, or physiological location of the expression of the gene interest based upon the sequence-specific hybridization detected in step (c).

11. The method of claim 10, wherein in step (a) is provided a substrate having a plurality of DNA probes arranged in an array.

12. The method of claim 10, wherein in step (a) is provided a substrate having a plurality of DNA probes arranged in an array.

13. The method of claim 10, wherein in step (b), the substrate is contacted with a sample containing cDNA.

14. The method of claim 10, wherein in step (b), the substrate is contacted with a sample containing mRNA.

15. The method of claim 10, wherein in step (c) the substrate is analyzed by surface plasmon resonance imaging.

16. The method of claim 10, wherein step (b) further comprises boiling the sample for a period of time sufficient to denature the mRNA or cDNA present in the sample before contacting the substrate to the sample.

17. The method of claim 10, wherein step (b) further comprises fragmenting the mRNA or cDNA present in the sample before contacting the substrate to the sample.

18. The method of claim 17, wherein the nucleic acids present in the sample are fragmented by applying sufficient pressure to the sample cause nucleic acid fragmentation.

19. The method of claim 17, wherein the nucleic acids present in the sample are fragmented by heating the sample to a sufficient temperature and for a sufficient amount of time to cause nucleic acid fragmentation.

20. A method of detecting and quantifying sequence-specific hybridization of nucleic acids comprising:
   (a) depositing an ω-modified alkanethiol monolayer on a metal substrate;
   (b) reacting hydrophobic protecting groups with the monolayer;
   (c) patterning the monolayer to create an array of exposed metal substrate areas;
   (d) depositing ω-modified alkanethiol in the areas of exposed metal substrate, thereby yielding an array of discrete, unprotected ω-modified alkanethiol spots;
   (e) attaching nucleic acid probes to the discrete, unprotected ω-modified alkanethiol spots, thereby yielding an array of discrete spots having nucleic acid probes immobilized thereon;
   (f) removing the protecting groups of step (b); and
   (g) making the monolayer resistant to non-specific protein binding; and then
   (h) contacting the substrate of step (g) with a sample known to, or suspected of, containing target nucleic acids at a concentration not greater than 500 nM, under conditions and for a time sufficient for sequence-specific hybridization to occur between target nucleic acids present in the sample and the nucleic acid probes immobilized on the substrate; and then
   (i) analyzing the substrate by surface plasmon resonance, whereby sequence-specific hybridization between the target nucleic acids present in the sample and the nucleic acid probes immobilized on the substrate is detected.

21. The method of claim 20, wherein in step (e), DNA molecules are attached to the discrete, unprotected ω-modified alkanethiol spots.

22. The method of claim 20, wherein in step (e), RNA molecules are attached to the discrete, unprotected ω-modified alkanethiol spots.

23. The method of claim 20, wherein in step (h), the substrate is contacted with a sample containing DNA.

24. The method of claim 20, wherein in step (h), the substrate is contacted with a sample containing RNA.

25. The method of claim 20, wherein in step (h), the substrate is contacted with a sample containing ribosomal RNA.

26. The method of claim 20, wherein in step a) the ω-modified alkanethiol monolayer is deposited on a gold substrate.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is A or C

<400> SEQUENCE: 1
agagtttgat cntggctcag                    20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is G or T
<220> FEATURE:
<221> NAME/KEY: misc_feature
<222> LOCATION: (3)..(3)
<223> OTHER INFORMATION: n is C or T

<400> SEQUENCE: 2
ggntaccttg ttacgactt                     19

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gtccccctct ttggtcttgc                    20

<210> SEQ ID NO 4

```
-continued

<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 4
ctccccgctg aaagta                                                    16

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
cggtgcttct tctgc                                                     15

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
cttttatgtt tgaaccatgc g                                              21

<210> SEQ ID NO 7
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 7
ttccctaaca acagag                                                    16

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 8
cgtggctttc tggtta                                                    16

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 9
actgctgcct cccgtag                                                   17

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
```

```
ggatgtgtgt ggagtgttag aaag                                          24

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
gccgaagcca ccttttat                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ataaaaggtg gcttcggc                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
gccagcttat tcaactag                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
ctagttgaat aagctggc                                                 18
```